US008163789B2

(12) United States Patent
Doemling

(10) Patent No.: US 8,163,789 B2
(45) Date of Patent: Apr. 24, 2012

(54) SELECTIVE AND DUAL-ACTION P53/MDM2/MDM4 ANTAGONISTS

(75) Inventor: Alexander Doemling, Pittsburgh, PA (US)

(73) Assignee: University of Pittsburgh—of the Commonwealth System of Higher Education, Pittsburgh, PA (US)

( * ) Notice: Subject to any disclaimer, the term of this patent is extended or adjusted under 35 U.S.C. 154(b) by 971 days.

(21) Appl. No.: 12/106,280

(22) Filed: Apr. 19, 2008

(65) Prior Publication Data
US 2008/0280769 A1   Nov. 13, 2008

Related U.S. Application Data

(60) Provisional application No. 60/907,902, filed on Apr. 20, 2007, provisional application No. 60/960,516, filed on Oct. 2, 2007.

(51) Int. Cl.
*A61K 31/4174* (2006.01)
*A61K 31/4178* (2006.01)
*C07D 233/64* (2006.01)

(52) U.S. Cl. ..................... 514/397; 548/311.1

(58) Field of Classification Search ............... 548/311.1; 514/397
See application file for complete search history.

(56) References Cited

OTHER PUBLICATIONS

Gelens et al, Molecular Diversity (2006), vol. 10, pp. 17-22.*
Franck Toledo et al., "Regulationg the p53 pathway: in vitro hypotheses, in vivo veritas", Nature Reviews, Cancer, vol. 6, Dec. 2006, pp. 909-923.
Robin S. Bon et al., "Novel Multicomponent Reaction for the Combinatorial Synthesis of 2-Imidazolines", Organic Letters, vol. 5, No. 20, 2003, pp. 3759-3762.
Claudio Palomo et al., "Asymmetric Synthesis of β-Lactams by Staudinger Ketene-Imine Cycloaddition Reaction", Eur. J. Org. Chem. 1999, 3223-3235.
Alexander S. Kiselyov et al., "Solid Support Synthesis of Polysubstituted Tetrahydro-quinolines via Three-Component Condensation Catalyzed by Yb(OTf)3.", Tetrahedron 54 (1998) 5089-5096.
Ka Young Lee et al., "A practical synthesis of N-tosylimines of arylaidehydes", Tetrahedron Letters 44, (2003) 1231-1234.
International Search Report PCT/US2008/004993.
Lyubomir T. Vassilev et al., "In Vivo Activation of the p53 Pathway by Small-Molecule Antagonists of MDM2", Science, vol. 303, Feb. 6, 2004, pp. 844-848.
Alexander Domling, "Recent Developments in Isocyanide Based Multicomponent Reactions in Applied Chemistry", Chem. Rev. 2006, 106, 17-89.
Walfrido Antuch et al., "Design and modular parallel synthesis of a MCR derived α-helix mimetic protein—protein interaction inhibitor scaffold", Bioorganic & Medicinal Chemistry Letters 16 (2006) 1740-1743.

* cited by examiner

*Primary Examiner* — Kamal Saeed
*Assistant Examiner* — Janet L Coppins
(74) *Attorney, Agent, or Firm* — Stephen A. Bent; Foley & Lardner LLP

(57) ABSTRACT

A fragment-based strategy, involving "multicomponent reaction chemistry" (MCR), can identify novel chemotypes that disrupt the p53/MDM2 or p53/MDM4 complex employs. This approach uses high resolution structural information to delineate the region of a first protein or a ligand that is nestled within the binding pocket of a second target protein. The identified region is imported into a database containing MCR scaffolds to generate a virtual library of compounds, which subsequently are docked into the binding pocket of the target protein. Results from docking then are used to select compounds for synthesis and screening. A complementary, NMR-based methodology allows for screening the ability of compounds, selected using MCR, to disrupt the p53/MDM2 or p53/MDM4 complex.

4 Claims, 5 Drawing Sheets

A  B

SELECTIVE AND DUAL-ACTION P53/MDM2/MDM4 ANTAGONISTS

CROSS-REFERENCE TO RELATED PATENT APPLICATIONS

This application claims the benefit of U.S. Provisional Application No. 60/907,902, filed Apr. 20, 2007, and U.S. Provisional Application No. 60/960,516 filed Oct. 2, 2007, which are fully incorporated by reference.

BACKGROUND OF THE INVENTION

The occurrence of many human cancers can be linked to impaired nonfunctional p53 protein. The p53 protein is a tumor suppressor encoded by a gene whose disruption is associated with about 50% of all cancers. The p53 protein acts as a checkpoint in the cell cycle, either preventing or initiating programmed cell death. Additionally, p53 protein is also involved in the development of tumors that have become resistant to treatment. It therefore appears that p53 plays a key role in the controlling the progression of cancer.

p53 is a transcription factor whose ability to initiate programmed cell death is most often repressed in cancer. Of the variety of biological molecules that are capable of inactivating p53, the oncoprotein MDM2 is believed to be the main negative regulator of this protein. Additionally, MDM2/p53 association has been implicated to play a role in drug resistance that has become a major problem in anti-cancer therapy.

The present invention provides methodology for selecting compounds that are capable of antagonizing the p53/MDM2 interaction. Additionally, the invention provides a strategy for overcoming negative regulator-dependant cancer resistance in vitro, cell-based, and xenograft models. Of the several classes of antagonists have been developed, the most prominent and best investigated are the nutlins.

Recently, another p53-binding protein, MDM4 (MDMX) has gained increasing attention as an equally important negative regulator of p53. In particular, a consensus exists that effective activation of p53-induced apoptosis must be based on a dual-action approach, involving both an MDM2 and an MDM4 antagonist. Thus, dual-action p53/MDM2/MDM4 antagonists "could be used to treat 2,000,000-3,000,000 new cancers each year, and so might represent an important class of anti-cancer drugs, assuming that their therapeutic index is acceptable." Toledo & Wahl (2006). See Wahl et al., *Nat. Rev. Cancer* (2006), 6, 909.

Yet neither small molecular weight MDM4 inhibitors nor dual-action MDM2/MDM4 antagonists have been identified. Additionally, a high resolution structure of p53 bound to the MDM4 protein has not been published, which precludes the development of molecules capable of inhibiting or disrupting the p53/MDM4 interaction.

SUMMARY OF THE INVENTION

In accordance with one aspect of the invention, therefore, a method is provided for identifying a compound that disrupts protein-protein interaction. The inventive method comprises (A) identifying a region of a first protein that interacts with a binding region a second protein using high resolution structural data; (B) incorporating a fragment of the identified region from step (A) into a database comprising multi-component reaction scaffolds to generate a library of molecules that incorporate the fragment; (C) docking the molecules from step (B) into a high resolution structure of the second protein; and (D) analyzing the results from step (C) to identify a compound that disrupts protein-protein interaction.

In another aspect, the invention provides a method for screening compounds that antagonizes MDM2/p53 or MDM4/p53 complex. To this end, the method of the invention comprises (A) contacting the complex with a compound to be screened and (B) obtaining a NMR of the complex in (i) the presence and (ii) absence of the compound, such that changes in the NMR spectrum are revealed, where the spectral changes result from a disruption the complex by the compound. In a preferred embodiment, the MDM2/p53 or MDM4/p53 antagonist is an imidazole, an imidazolidine, a β-lactam, a tetrahydroquinoline, a 2-aminomethyl phenol, or a 1-(alkylsulfonyl)-4,5,-dihydro-1H-imidazole.

In accordance with a further aspect of the invention, a compound is provided that antagonizes MDM2/p53 or MDM4/p53 complex and that is an imidazole, an imidazolidine, a β-lactam, a tetrahydroquinoline, a 2-aminomethyl phenol, or a 1-(alkylsulfonyl)-4,5,-dihydro-1H-imidazole. Illustrative of such a compound is one that conforms to formula I

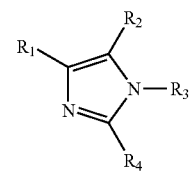

wherein

R1 is optionally substituted $(C_3-C_8)$aryl, $(C_3-C_8)$heterocycloalkyl, $(C_3-C_8)$heteroaryl, $(C_1-C_6)$alkyl$(C_3-C_8)$aryl, $(C_3-C_8)$aryl$(C_1-C_6)$alkyl, optionally substituted benzyl, $(C_3-C_8)$cycloalkyl$(C_1-C_6)$alkyl and $(C_3-C_8)$cycloalkyl;

R2 is optionally substituted $(C_3-C_8)$aryl, optionally substituted $(C_3-C_8)$heteroaryl, optionally substituted $(C_3-C_8)$heterocycloalkyl, $(C_3-C_8)$heteroaryl$(C_1-C_6)$alkyl and $(C_3-C_8)$heterocycloalkyl$(C_1-C_6)$alkyl;

R3 is optionally substituted $(C_3-C_8)$aryl, aryl$(C_1-C_6)$alkyl, optionally substituted benzyl, and $(C_3-C_8)$cycloalkyl$(C_1-C_6)$alkyl;

R4 is optionally substituted $(C_1-C_8)$alkyl, NRR'$(C_1-C_8)$alkyl; and

R and R' are independently selected from the group consisting of hydrogen, $(C_1-C_8)$alkyl and $(C_3-C_8)$cycloalkyl. Preferred embodiments in this regard are the compounds:

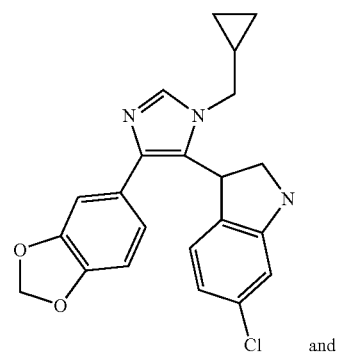

and

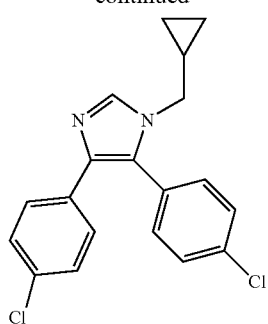

Likewise illustrative of a compound of the invention is one that conforms to formula II or to an stereoisomer thereof:

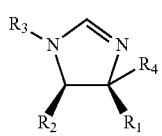
II wherein

R1 is straight or branched optionally substituted ($C_1$-$C_8$) alkyl, optionally substituted ($C_3$-$C_8$)aryl, ($C_1$-$C_8$alkyl)-S—($C_1$-$C_8$alkylene), aryl($C_1$-$C_6$)alkylene, ($C_3$-$C_8$)aryl($C_1$-$C_6$) alkyl, optionally substituted benzyl, ($C_3$-$C_8$)cycloalkyl($C_1$-$C_6$)alkylene, optionally substituted ($C_3$-$C_8$)aryl and ($C_3$-$C_8$) cycloalkyl;

R2 is optionally substituted ($C_3$-$C_8$)aryl, optionally substituted ($C_3$-$C_8$)heteroaryl, fused or unfused ($C_3$-$C_8$)heteroaryl;

R3 is optionally substituted ($C_1$-$C_8$)alkyl, optionally substituted ($C_3$-$C_8$)aryl, aryl($C_1$-$C_6$)alkylene, optionally substituted benzyl, ($C_3$-$C_8$)cycloalkyl($C_1$-$C_6$)alkylene, ($C_3$-$C_8$)cycloalkyl, ($C_3$-$C_8$)heterocycloalkyl, heteroaryl and ($C_3$-$C_8$) heterocycloalkyl($C_1$-$C_6$)alkylene, ($C_3$-$C_8$)cycloalkyl($C_1$-$C_6$) alkylene, ($C_1$-$C_8$ alkyl)-X—($C_1$-$C_8$)alkylene;

X is O or N;

R4 is selected from the group consisting of C(O)OR, C(O)NR'R' and C(O)Z;

R is selected from the group consisting of hydrogen and ($C_1$-$C_6$)alkyl;

R' and R" are independently selected from the group consisting of hydrogen, ($C_1$-$C_8$)alkyl, ($C_1$-$C_8$ alkyl)-O—($C_1$-$C_8$) alkylene, ($C_3$-$C_8$)cycloalkyl; ($C_1$-$C_8$)alkyl($C_3$-$C_8$)heterocycloalkylene, ($C_3$-$C_8$)heteroaryl($C_1$-$C_6$)alkylene, ($C_3$-$C_8$) heterocycloalkyl and ($C_3$-$C_8$)heterocycloalkyl($C_1$-$C_6$) alkylene; and Z is a ($C_3$-$C_8$)heterocycloalkyl.

Preferred compounds under formula II are selected from the group consisting of:

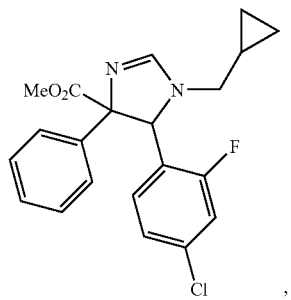

,

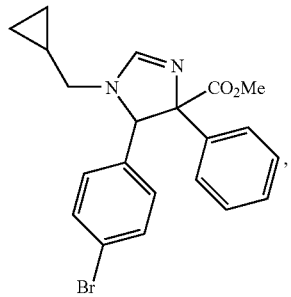

,

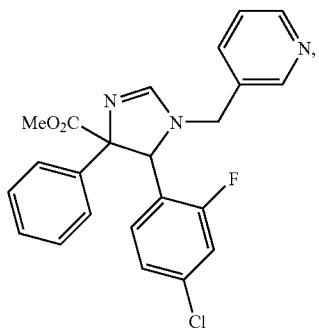

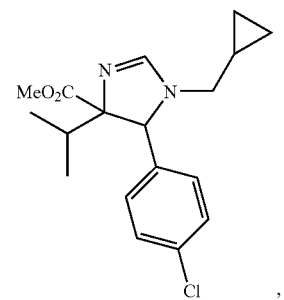

,

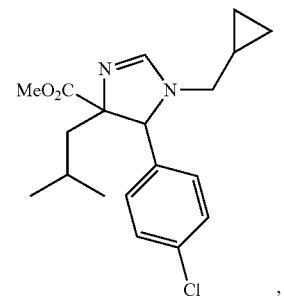

,

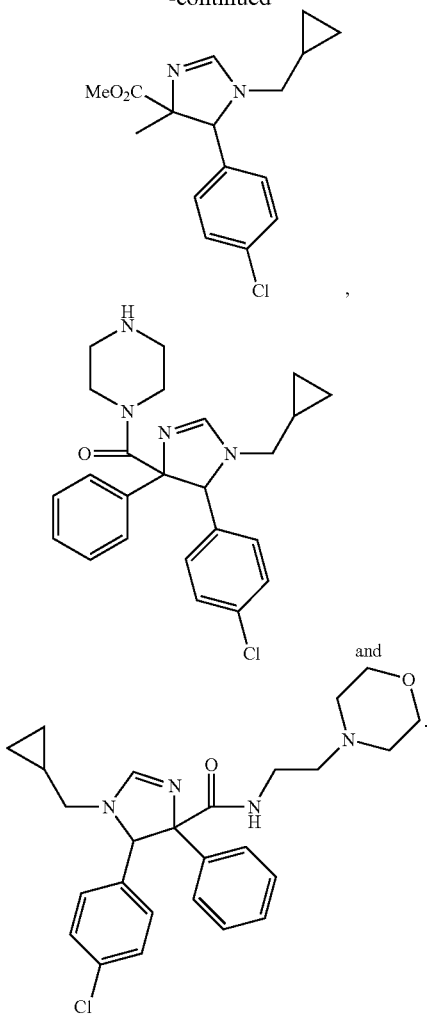

, and

DETAILED DESCRIPTION OF THE PREFERRED EMBODIMENTS

Figure 1:
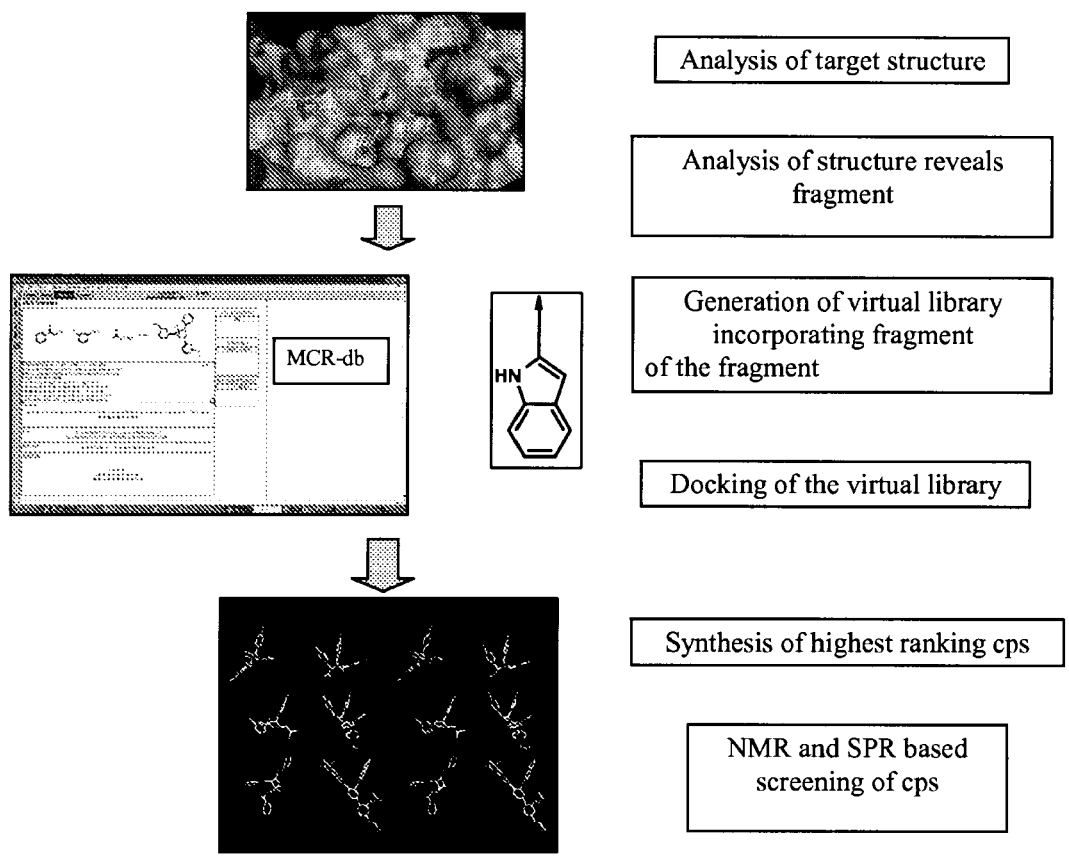
FIG. 1 is a schematic representation that illustrates the sequence of steps involved in the identification and ranking of virtual library compounds capable of binding to a protein target of interest.

Unless indicated otherwise, the terms and phrases used in this description have the following meanings:

"Alkyl" refers to a straight or branched chain, saturated hydrocarbon having the indicated number of carbon atoms. For example, ($C_1$-$C_6$)alkyl is meant to include, but is not limited to methyl, ethyl, propyl, isopropyl, butyl, sec-butyl, tert-butyl, pentyl, isopentyl, neopentyl, hexyl, isohexyl, and neohexyl. An alkyl group can be unsubstituted or optionally substituted with one or more substituents as described herein throughout.

The term "aryl" refers to a 6- to 14-membered monocyclic, bicyclic or tricyclic aromatic hydrocarbon ring system. Examples of an aryl group include phenyl and naphthyl. An aryl group can be unsubstituted or optionally substituted with one or more substituents as described herein throughout.

"Cycloalkyl" denotes a 3- to 14-membered saturated or unsaturated non-aromatic monocyclic, bicyclic or tricyclic hydrocarbon ring system. Included in this class are cycloalkyl groups which are fused to a benzene ring.

The term "heteroaryl" refers to an aromatic heterocycle ring of 5 to 14 members and having at least one heteroatom selected from nitrogen, oxygen and sulfur, and containing at least 1 carbon atom, including monocyclic, bicyclic, and tricyclic ring systems. Representative heteroaryls are triazolyl, oxadiazolyl, pyridyl, furyl, benzofuranyl, thiophenyl, benzothiophenyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, quinazolinyl, pyrimidyl, azepinyl, oxepinyl, quinoxalinyl and oxazolyl. A heteroaryl group can be unsubstituted or optionally substituted with one or more substituents as described throughout.

The term "heterocycle" refers to 3- to 14-membered ring systems that are either saturated, unsaturated, or aromatic, and that contains from 1 to 4 heteroatoms independently selected from nitrogen, oxygen and sulfur, where the nitrogen and sulfur heteroatoms can be optionally oxidized and the nitrogen heteroatom can be optionally quaternized, including monocyclic, bicyclic, and tricyclic ring systems. The bicyclic and tricyclic ring systems may encompass a heterocycle or heteroaryl fused to a benzene ring. The heterocycle can be attached via any heteroatom or carbon atom. Heterocycles include heteroaryls as defined above.

Unless otherwise stated, the term "heterocycloalkyl," by itself or combined with other terms, represents cyclic versions of "heteroalkyl." Additionally, a heteroatom can occupy the position at which the heterocycle is attached to the remainder of the molecule.

The present inventors have developed a strategy for rapidly identifying and screening novel chemotypes capable of inhibiting protein targets. Their fragment-based drug discovery approach, called "multicomponent reaction chemistry" (MCR), provides an elegant and rapid way to identify suitable molecular scaffolds as potential therapeutic compounds for disrupting or inhibiting the activity of a specific protein. MCR. See Doemling et al., Chem. Rev. (2006), 126, 18-78.

According to one aspect of the present invention, high resolution X-ray or NMR structural data from the Protein Data Bank was used to define the sequence of residues that are involved in protein-protein interactions. Alternatively, structural data relating to enzyme-substrate complexes can also be used to identify the fragment of the substrate involved in binding to the active site of an enzyme. This information is then imported into a database containing MCR scaffolds to generate a virtual library of compounds that incorporate the salient feature of the fragment identified using structural data. This virtual library then is docked into the high-resolution structure of the protein target of interest and the highest ranking virtual hits are inspected manually for structural consistency and energy requirements to binding. This allows the generation of a list of the most promising compounds that are synthesized in the lab and screened for activity (FIG. 1).

Figure 2A:
FIG. 2A shows picture of p53 peptide (stick representation) bound to MDM2.
Figure 2B:
FIG. 2B shows picture of p53 peptide (stick representation) bound to MDM4.
Figure 3:
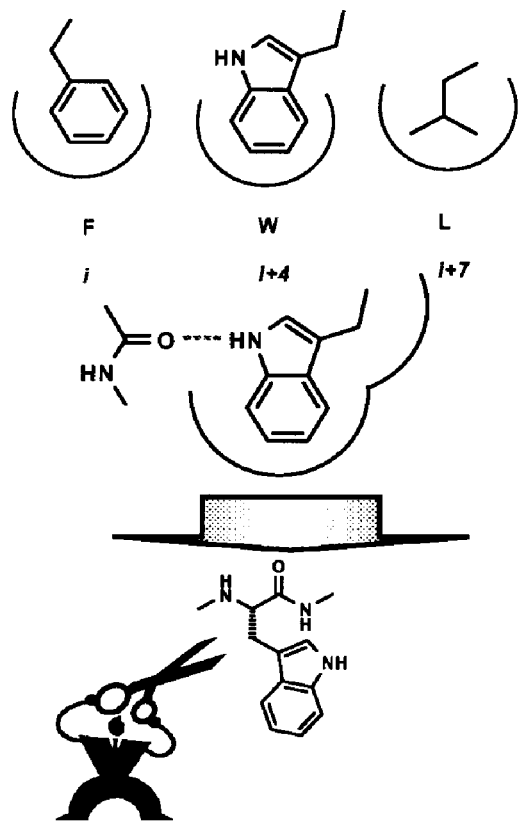
FIG. 3 is a graphical representation showing the position of the amino acid triad (F, W, L) in the binding pocket of p53.

This approach has been applied to identify compounds that are capable of selectively disrupting the protein-protein interactions (PPI) between the transcription factor p53 and its negative regulators MDM2 or MDM4, which are of high relevance to cancer treatment. FIGS. 2A and 2B pictorially depict the interactions of the key residues of a 15-amino acid peptide fragment of p53 in the binding sites of MDM2 and MDM4 as deduced from the X-ray coordinates of a high-resolution crystal structure of the protein-peptide complex. Analysis of the p53/MDM2 structural data revealed that the indole ring of tryptophan would be a suitable fragment for generating a virtual library using the database of MCR scaffolds that contain an indole ring. As seen in FIG. 3, three amino acids of the p53 peptide fragment, phenylalanine, tryptophan and leucine, are within the binding pocket of MDM2 and are therefore important for protein-peptide binding interactions. Of these, the indole side chain of tryptophan that rests in a hydrophobic pocket of MDM2 was selected as a suitable fragment modifications and generation of virtual libraries.

Figure 4:
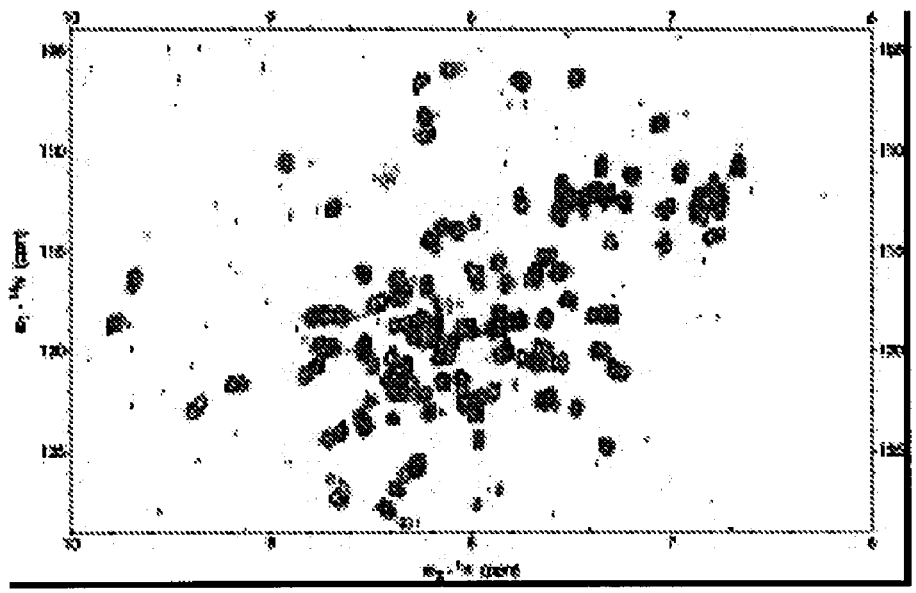
FIG. 4 shows a $^1$H-$^{15}$N-HSQC 600 MHz spectra of MDM2 in the presence (red) and absence (blue) of MDM2 binder.
Figure 5:
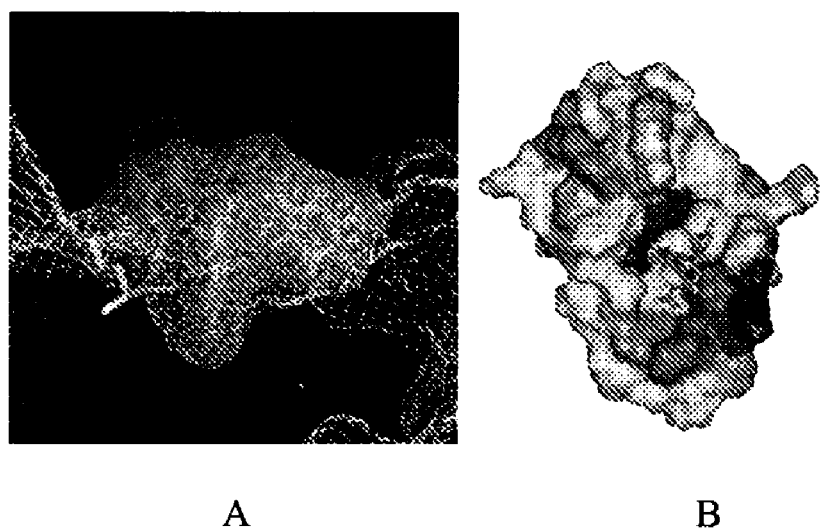
FIG. 5A shows the predicted orientation for an imidazole in the binding pocket of MDM2.
FIG. 5B shows the observed binding mode based on X-ray crystal data.

In one of its aspects, the present invention provides a method for generating and screening virtual libraries based on 40 different MCRs having the indole fragment. The inventive method comprises docking individual molecules from the virtual library into a high resolution structure of the MDM2 protein. Docking is carried out by maintaining the same positional constraints on the indole ring of the docked molecule to those for the indole side chain in the high resolution X-ray structure of MDM2-p53 peptide. The compounds identified from docking experiments as potential inhibitors of MDM2-p53 interaction are then synthesized and tested for the inhibitory activity using an NMR-based binding assay. FIG. 4 shows a 2D-NMR spectra of fully labeled $^{15}N$ MDM2 in the presence and absence of p53 peptide and correlates the changes in NMR chemical shifts as a result of binding of the p53 peptide, ($^{1}H$-$^{15}N$-HSQC 600 MHz spectra with (red) and without (blue) MDM2 binder). A similar strategy was used to identify and select compounds that could potentially be used as inhibitors for disrupting MDM4-p53 interaction.

Such an NMR-based screen has many advantages. For example, this screening method allows for the rapid determination of an approximate $K_A$ for the small molecule inhibitors, with the possibility of obtaining a more accurate $K_A$ value at a later time by titrating the p53-MDM2 complex using increasing concentrations of the inhibitor of interest. A second advantage of using this technique is that it allows identification of the binding site of the small molecule in the target protein by investigating the chemical shift perturbations that occur on binding. This information can then be used to further refine the chemical scaffold with an aim towards improving the affinity of the molecule for its target. Finally, NMR-based screening yields valuable information about promiscuous inhibitors which act as false positives by precipitating the target protein through hydrophobic effects. This information is not available when classical screening approaches such as fluorescence polarization or ELISA type assays are used for screening. Importantly, using the claimed NMR-screening technique the inventors have were able to identify that some of the known compounds claimed to antagonize p53/MDM2 do not actually bind MDM2.

To verify further that ability of the identified inhibitor molecules to disrupt protein-p53 interaction, a secondary NMR based assay was used to determine the dissociation constant ($K_D$) of p53 from MDM2. According to the claimed screening method, a sample of p53-MDM2 is titrated using increasing concentrations of the potential inhibitor molecule and the $K_D$ is obtained from the chemical shift perturbations. The NMR based screening method, together with cellular assays, allowed the identification of individual molecules within a family of compounds that needed further follow-up.

In accordance with the invention, Table 1 lists promising chemotypes that were identified as antagonists of the p53/MDM2 complex. As mentioned later in this application, some of the compounds showed a dose dependant up regulation of p53 in ex-vivo cell based assays with one particular compound capable of disrupting the p53/MDM2 complex in the NMR tube at a nanomolar concentration.

TABLE 1

| no | MCR backbone | MCR |
|---|---|---|
| 1 | 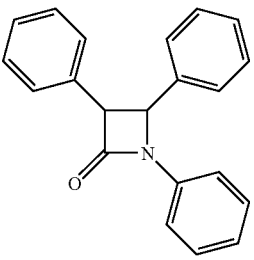 | Staudinger-3CR |
| 2 | 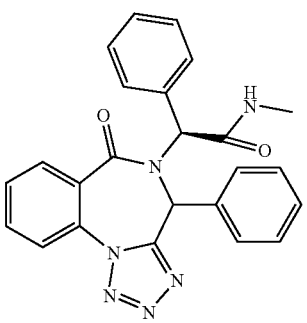 | U-4CR (UDC) |

TABLE 1-continued

| no | MCR backbone | MCR |
|----|--------------|-----|
| 3 | | U-4CR(UDC)-DKP formation |
| 4 | | U-4CR (UDC) |
| 5 | | U-4CR |
| 6 | | MCR |
| 7 | | Orru-3CR + novel MCR |

TABLE 1-continued

| no | MCR backbone | MCR |
|----|--------------|-----|
| 8 | (structure: 2-phenyl-3-phenyl-4-carboxy-3,4-dihydroisoquinolin-1(2H)-one) | MCR |
| 9 | (structure: iodo-indazolone with N-phenyl and N-CH(phenyl)C(O)NHMe) | U-4CR (UDC) |

The compounds identified using MCR were then screened for the ability to bind MDM2 or MDM4 ($K_A$) (primary assay). The molecules identified as binders of MDM2 or MDM4 by the primary assay are subsequently tested for their ability to disrupt the MDM2/p53-peptide complex ($K_D$) in a secondary assay. Based on the results from the primary and secondary assays, further downstream assays involving screening using various cell lines (PC3, A549, MDAMB231) and determination of the growth inhibition constants may be performed for a select sub-set of molecules. Western blot analysis of certain compounds is performed to determine p53, MDM2, and p21 content.

I. Compounds Having an Imidazole Scaffold

In one embodiment, the claimed MCR predicted compounds having an imidazole scaffold to be particularly potent antagonists of MDM2 or MDM4/p53 interaction. According to the docking models used by the inventors, the p53 tryptophane mimicking indole has to be placed at position-5 of the imidazole ring. Table 2 summarizes the different compounds synthesized in this regard and their respective $K_A$ values.

Scheme 1 graphically depicts the synthesis of for this family of compounds. Synthesis to assemble the imidazole scaffold was carried out using the van Leusen 3-component reaction (CR) of a Tosmic derivative, an aldehyde and a primary amine under basic conditions to give the 1, 4, 5 substituted imidazoles. See van Leusen, *Org. React.* (2003), 7.

The derivatives synthesized using the above methodology had binding affinities for MDM2 in the µM range. Interestingly, the imidazole family of compounds had at least a 5-10 fold weaker binding affinity for MDM4. The accuracy of the predicted binding model was further tested by synthesizing a compound that was known to be too big to fit into the binding site of MDM2 as determined by the NMR. Molecules identified as potential binders by the NMR screen are then used as templates to improve the binding properties of the next generation of imidazole analogs. It was found using the methodology of the instant invention that introducing a substituent at position-2 of the imidazole ring would promote the lipophilicity as well as the water solubility of this family of compounds.

Scheme 1

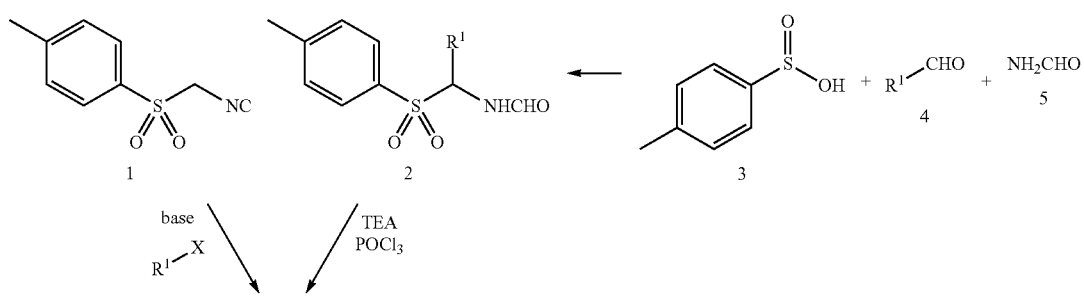

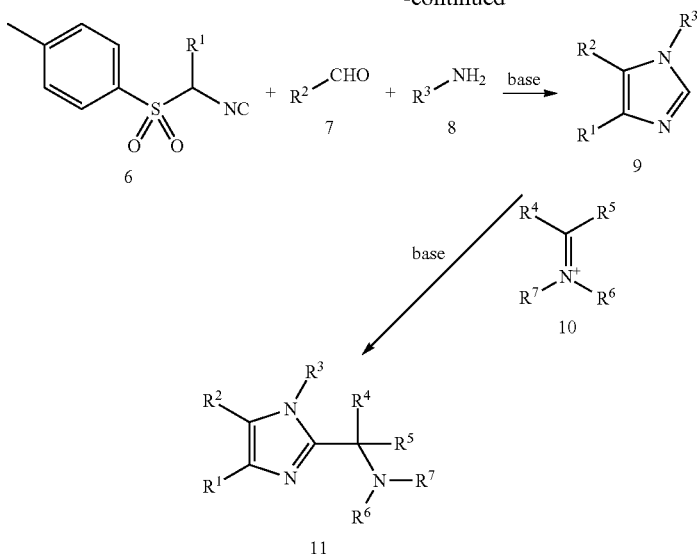

II. Compounds Having an Imidazolidine Scaffold

In yet another aspect, the claimed MCR method identified compounds having an imidazoline scaffold as potent antagonists of the p53/MDM2 or MDM4 interaction. The imidazolidine derivates were synthesized using a three component reaction involving an isocyanide ester of an α-amino acid, an aldehyde and a primary amine as shown in Scheme 2 using a published method. See Bon, R. S., et al., *Org. Lett.* (2003), 5, 3759. The observed affinities for synthesized analogs were in the low μM range when diasteriomeric mixtures enriched in the syn isomer were used in the screen (Scheme 3). However, separation of the two diastereoisomers for one representative analog showed that the syn-isomer had a higher affinity for MDM2 than the observed binding affinity for the diasteromeric mixture. Confirmation about the higher potency of the syn-isomer was obtained by synthesizing each isomer of BEB116 (Scheme 4), and testing the ability of each isomer to interrupt the p53/MDM2 complex. The result confirmed the original observation that the syn-isomer has higher potency. Of significance is the observation that compounds identified using MCR have a lower molecular weight than nutlin-3, the known potent antagonist of p53/MDM2 complex. Thus, the subject imidazolidine analogs are suitable for formulations for oral delivery.

Scheme 2

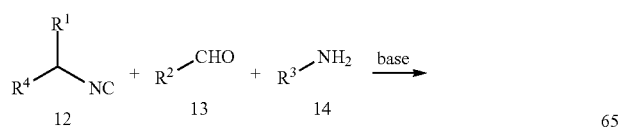

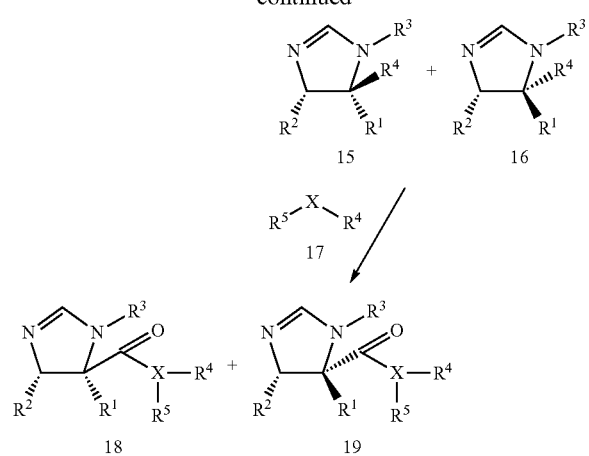

Scheme 3

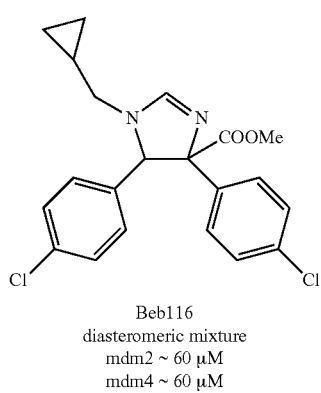

Beb116
diasteromeric mixture
mdm2 ~ 60 μM
mdm4 ~ 60 μM

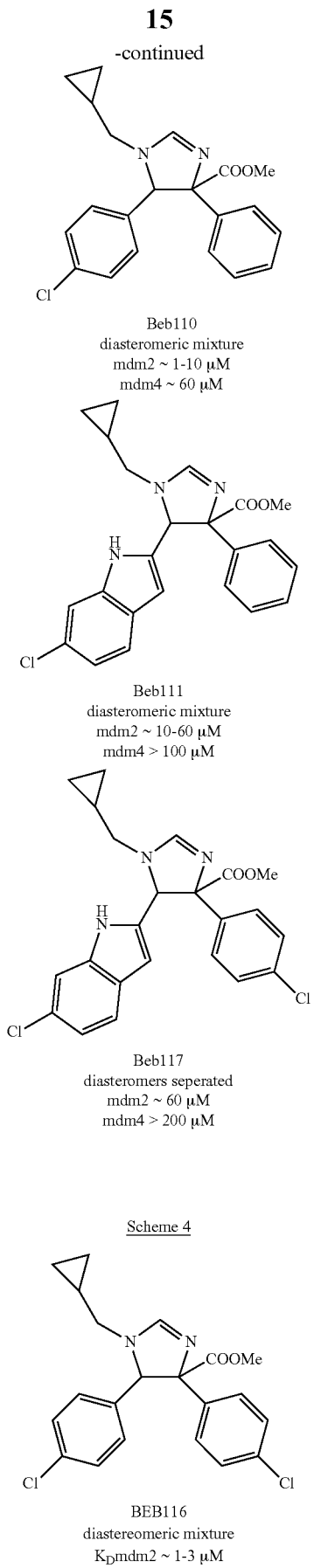

Beb110
diasteromeric mixture
mdm2 ~ 1-10 μM
mdm4 ~ 60 μM

Beb111
diasteromeric mixture
mdm2 ~ 10-60 μM
mdm4 > 100 μM

Beb117
diasteromers seperated
mdm2 ~ 60 μM
mdm4 > 200 μM

Scheme 4

BEB116
diastereomeric mixture
$K_D$mdm2 ~ 1-3 μM

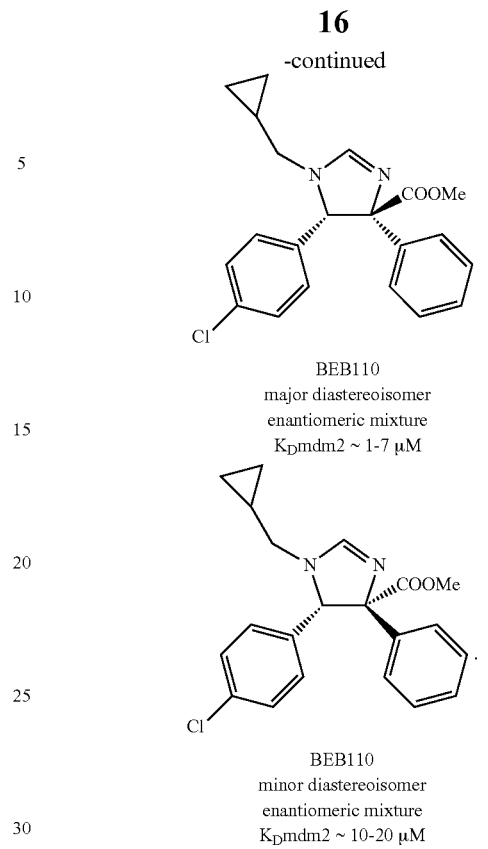

BEB110
major diastereoisomer
enantiomeric mixture
$K_D$mdm2 ~ 1-7 μM

BEB110
minor diastereoisomer
enantiomeric mixture
$K_D$mdm2 ~ 10-20 μM

III. The β-Lactam (Azetidione) Scaffold

Figure 6:
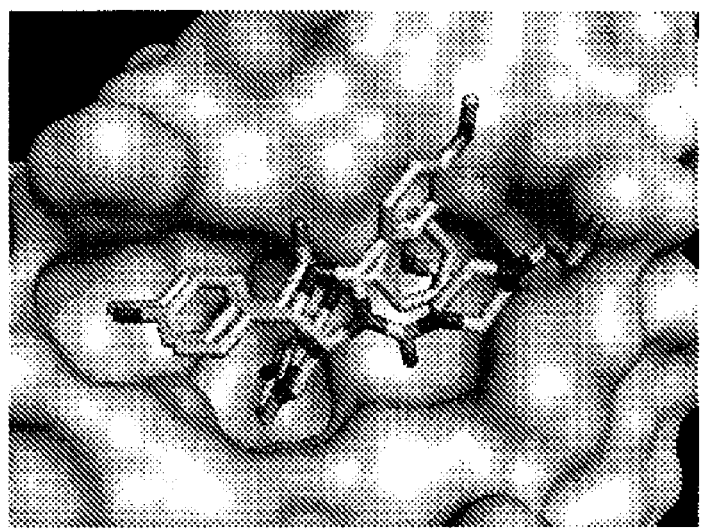
FIG. 6 shows the predicted binding mode of azetidinone scaffold (light blue sticks) to MDM2. An overlap of nutlin-3 (green sticks) is shown.

Pursuant to a further aspect of the invention, β-lactams provide another scaffold for designing potent antagonists of the p53/MDM2 or MDM4 complex. Compounds having the azetidinone scaffold were synthesized using a stereospecific Staudinger 3-CR method, involving an acylchloride, a primary amine and a ketone or an aldehyde as shown in Scheme 5. See Palomo, C., et al., *Eur. J. Org. Chem.* (1999), 8, 3223. The results from docking studies revealed that substituents at positions 1, 3 and 4 of the β-lactam ring would mimic the side chains of the F, W and L amino acids of p53. FIG. 6 shows a representation for the predicted binding mode for the azetidione scaffold to MDM2. Also depicted is an overlay of the known antagonist Nutlin-3. As seen in FIG. 6, there is a remarkable overlap between the azetidione and Nutlin-3 structures. Based on the predicted binding model, derivatives at positions 3- and 4- of the azetidione scaffold were predicted to increase affinity and water solubility. The affinity for some representative examples of this family of compounds are provided in Scheme 6.

Scheme 5

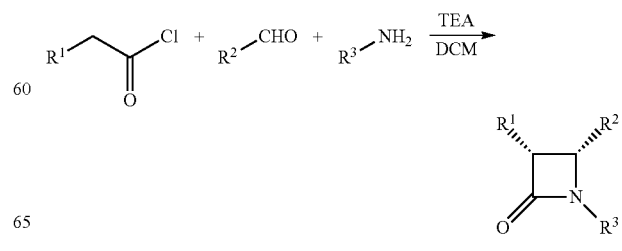

Scheme 6

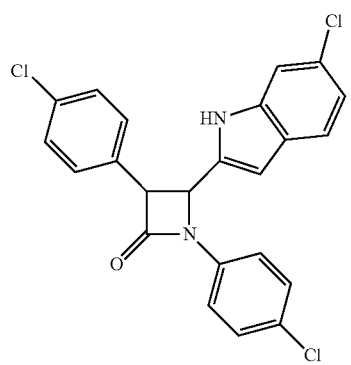

SS_43D
diastereomeirc mixture
mdm2 ~ 60 µM
mdm4 (-)

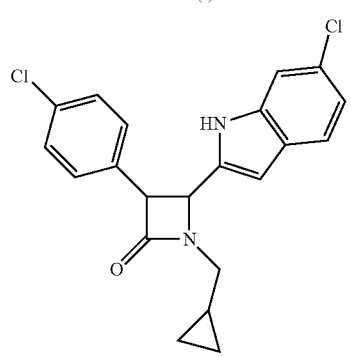

SS-87B-1
diastereomeirc mixture
mdm2 (sp)
mdm4 > 200 µM

IV. Tetrahydroquinoline Scaffold

Figure 7:
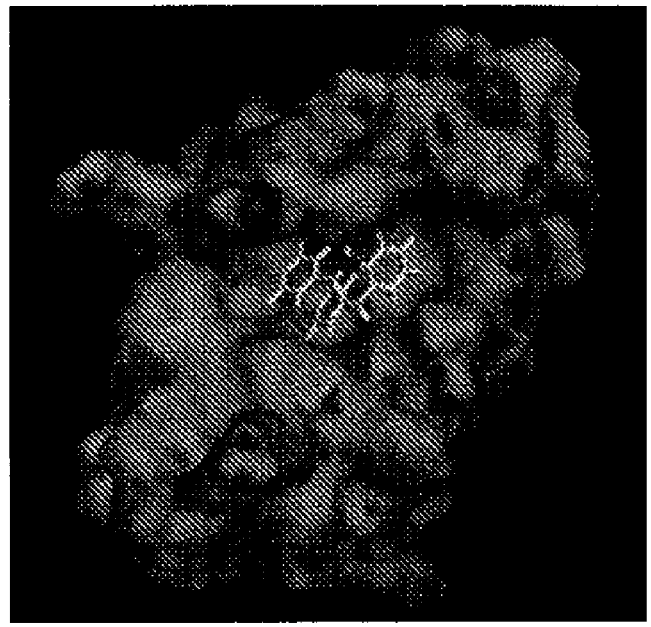
FIG. 7 shows the proposed binding mode of tetrahydroquinoline scaffold to MDM2.

In another aspect, the present invention allows the synthesis and testing of tetrahydroquinoline analogs as inhibitors of p53/MDM complex. A published procedure involving a three component reaction system was used for stereospecific synthesis of syn-2,4-disubstituted tetrahydroquinolines as shown in Scheme 7. See Kiselyov, A. S., et. al., *Tetrahedron* (1998), 54, 5089. FIG. 7 shows the predicted binding of the disubstituted tetrahydroquinolines to the active site of MDM2, while Scheme 8 shows some representative examples. Based on the predicted binding mode and results from screens involving some key derivatives a repertoire of analogs will be made and tested. Of particular interest is the ease for derivatizing this scaffold at the reactive secondary amine, which also promotes the water solubility for this family of compounds.

Scheme 7

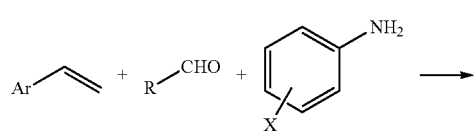

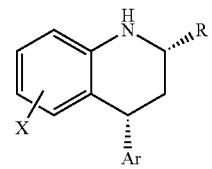

Scheme 8

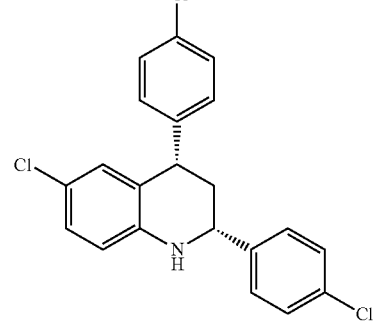

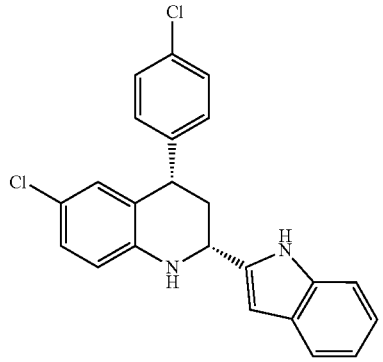

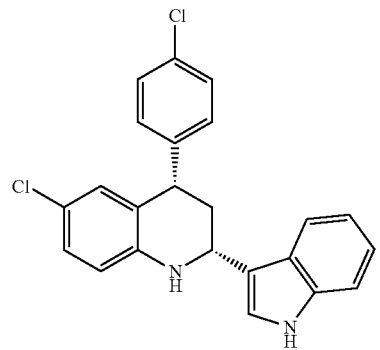

activity currently not yet measured

V. Betti Scaffold

In yet another embodiment of the invention, 2-aminomethyl phenols are scaffolds for designing MDM2-p53 and MDM4-p53 complex inhibitors. The target scaffold is synthesized using the Betti reaction that involves a reaction between a phenol, an aldehyde and a primary or secondary amine as depicted in Scheme 9. Some representative members for this family of compounds are shown in Scheme 10, along with their respective binding affinities for MDM2 and MDM4.

Scheme 9

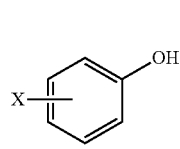
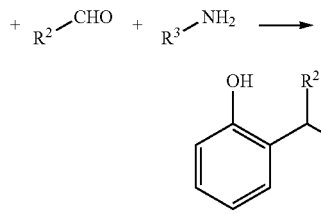

Scheme 10

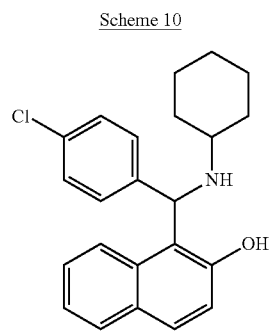

SS_85A
mdm2 ~ 60 μM
mdm4 > 200 μM

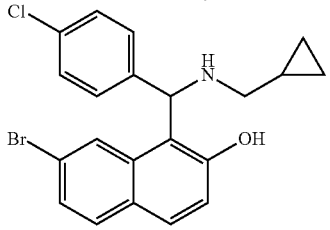

SS-92C-1
mdm2 (sp)
mdm4 > 200 μM

VI. 1-(Alkylsulfonyl)-4,5-dihydro-1H-imidazole scaffold (VI)

Figure 8:
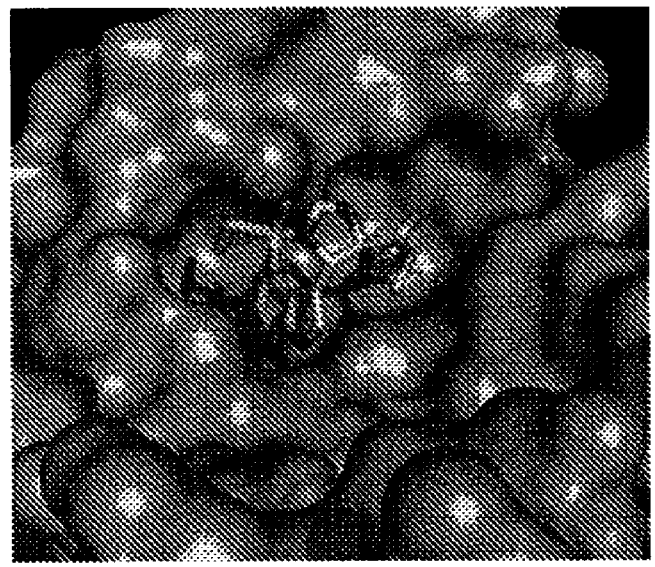
FIG. 8 shows the proposed binding mode of 1-alkylsulfonyl imidazolidines to MDM4.

In another embodiment, the 1-(Alkylsulfonyl)-4,5-dihydro-1H-imidazoles analogous to scaffold II are scaffolds for designing MDM2/p53 and MDM4/p53 complex inhibitors. The 1-alkysulfonylated imidazoles can be synthesized from the reaction of N-sulfonylated Schiff bases with isocyanates (Scheme 11). See Lee et al., *Tett. Lett.* (2003), 44, 1231-1234. Scaffold VI differs from scaffold II by the sharper angle between the imidazoline ring plane and the residue at 1-position. According to the proposed binding model (FIG. 8) it was predicted that scaffold VI would be especially useful for binding to MDM4 where the p53 leucine binding site is dramatically downsized as compared to MDM2 (FIG. 2).

Scheme 11

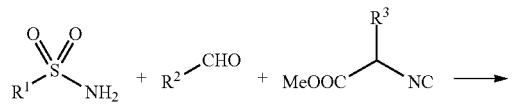

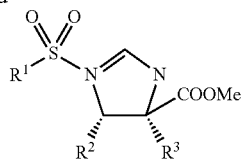
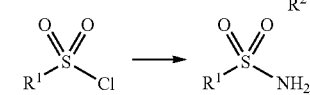

R$^1$     R$^2$     R$^3$

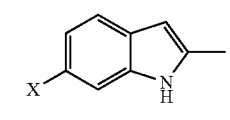

aliphatic (aromatic) α-aminoacids: Val, Leu, Ile, Met, Ala, Phe

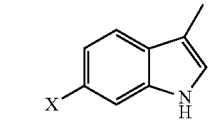

X = H, Cl, F, Br

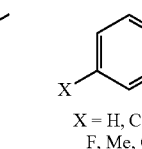
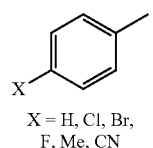

X = H, Cl, Br, F, Me, CN    X = H, Cl, Br, F, Me, CN    X = H, Cl, Br, F, Me, CN

The p53 tumor suppressor is a central element for regulation of cell cycle progression, DNA repair, and apoptosis and is an attractive cancer therapeutic target because its tumor suppressor activity can be stimulated to inhibit the growth of tumor cells. Not surprisingly, the p53 gene is mutated in ~50% of all human cancers. The remaining cancers retain wild-type p53 but the p53 pathway is inactivated or impaired through the interaction with negative regulators. A known negative regulator of p53 is MDM2.

MDM4 (MDMX) also has been recognized as an equally important, negative p53 regulator. Fluorescence in situ hybridization and immunohistochemistry studies reveal an increased MDMX copy number in ~65% of human retinoblastomas, with MDM2 being amplified in an additional 10% of these tumors that exclusively have wild-type p53.

Both MDM2 and MDM4 proteins cooperate in inactivation of p53. Recent studies showed that restoring p53 activity can halt the growth of cancerous tumors in mice, and in some cases, even cause tumors to disappear. Two groups constructed genetically engineered mice with an inducible p53 gene and oncogenic mutations that facilitate cancer development (lymphoma and sarcoma). After the mice developed tumors, the p53 gene was turned on, which initiated apoptosis and resulted in the shrinkage of the tumors.

So far, the best p53/MDM2 antagonist to be identified is nutlin-3. Several proof-of-concept in vivo models including SJSA-1 (osteosarcoma), MHM (osteosarcoma), LnCaP (prostate), 22Rv1 (prostate), and BC-3 (Kaposi's sarcoma herpesvirus induced lymphoma) xenografts demonstrate the ability of p53 to reduce or eliminate tumor growth.

Early clinical trials using adenovirus to carry a normal copy of p53 into tumors of patients with head and neck cancer or non-small cell cancer of the lung, led to reduced tumor growth or tumor shrinkage in some patients. Recently, Gendicine, another adenoviral vector for p53, has been approved for the treatment of patients with head-and-neck squamous cell carcinoma (HNSCC) in China. Interestingly, the group receiving a combination of Gendicine and radiotherapy for treatment, showed a 3-fold effect in complete tumor regression as compared with the group receiving radiotherapy alone.

Based on the ubiquitous occurrence of the dysfunctional p53 pathway in the majority of human cancers and the wealth of proof-of-concept studies in cells, xenograft models and humans, MDM2 and MDM4 are highly promising targets to fight cancer.

Each of the scaffolds shown below can be made by conventional synthesis. The underlying chemistry, generally, is straightforward to perform and does not require an inert gas atmosphere or dry conditions.

Certain scaffolds are produced as diastereomeric mixtures and were separated by well-known chiral chromatography or crystallization techniques. Compounds can be made on a 50-100 mg scale for analytical (NMR, HPLC-MS, HR-MS) and screening purposes. For compounds that require two-to-three step syntheses, the first intermediates can be prepared in larger quantities, e.g., 200-300 mg. Derivatives that show a high affinity for the protein were produced in larger quantities for xenograft screening. It is preferable that compounds of the invention have ≧95% purity as shown by HPLC, using UV/ELSC/TIC detectors and $^1$H-NMR, for example.

In accordance with the present invention, the affinities and water solubility can be refined for classes of identified antagonists of p53/MDM2/MDM4 binding.

Such compounds can be optimized by individually, synthesizing rather small libraries of 3-10 compounds per round. The chemistry tasks should be flexible to a certain degree, since the optimization process involves design and synthesis of compounds, screening of the compounds, and designing of a new round of compounds based on the results.

Illustrative in this regard are three scaffolds, whose affinities for MDM2 and MDM4 were increased as described in greater detail below.

Scaffold 1:

Pursuant to the present invention, the double digit micromolar binding affinity for the imidazole family of compounds was increased by at least three routes could be used to increase the affinity.

The first approach seeks to gain an additional hydrogen bonding site in the Phe binding pocket where an exposed backbone carbonyl of Asn$^{72}$ seems to be approachable. The inventors have determined that this carbonyl group can be addressed by an appropriately placed substituent at position-1 of the imidazole (the amine component). Accordingly, compounds such as 3-aminomethyl phenol, 3-aminomethyl aniline, 3-aminomethyl-cyclohexylamine, 3-aminomethyl-piperidine or similar compounds are disclosed as suitable precursors to approach this additional hydrogen bonding.

A second approach for increasing affinity, entails introducing substituents in the 2-position of the imidazole ring to gain additional van der Waals interaction and even water solubility. A substituent in the 2-position would mimic the interactions of the Leu (FSDLWKLL) in p53, which contributes additional van der Waals interactions in addition to FWL. Optimization of compounds that belong to this family was carried out as shown in Scheme 1. Table 2 lists representative analogs that were synthesized with their GI50 values against HCT116 cells in culture. The chemistry to accomplish substitution at position-2 of the immidazole ring would involve generation of the carbanion using LDA and subsequent alkylation with iminium salts or other alkylating agents.

A third approach for optimizing the affinity of this family of compounds involves substitutions at 5-position of the imidazole ring. The starting material for this position, according to one suitable synthetic route, are appropriately substituted p-toluene sulfonamides (Tosmic). Thus, several substituted phenyl Tosmics can be prepared and transformed to smaller libraries of imidazoles, according to the van Leusen chemistry as shown in Scheme 1.

TABLE 2

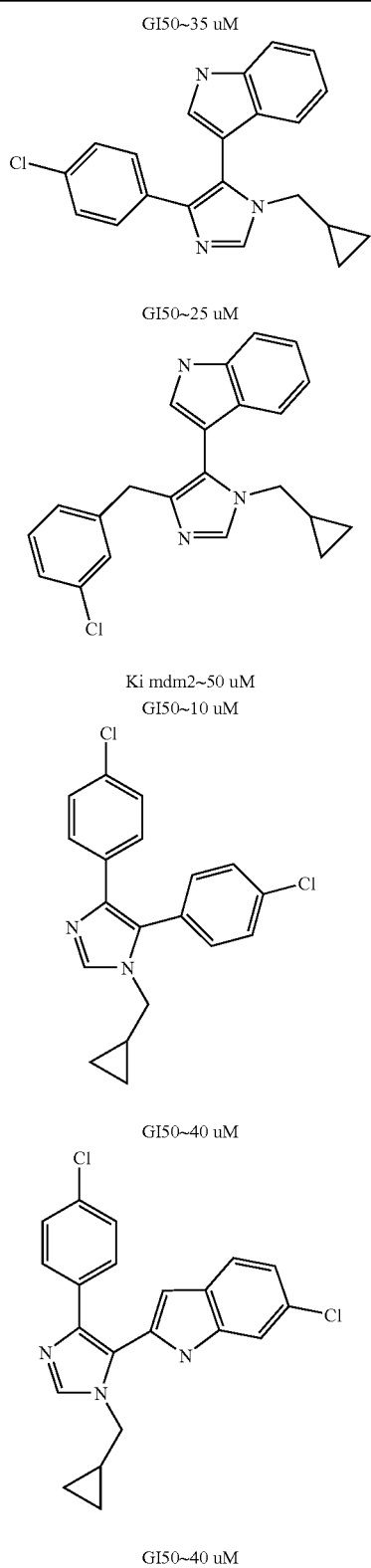

TABLE 2-continued
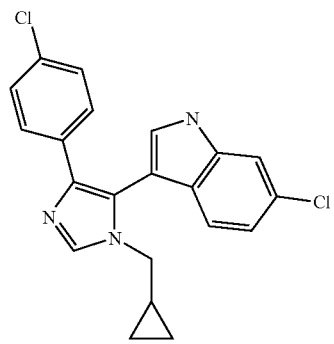
GI50~30 uM
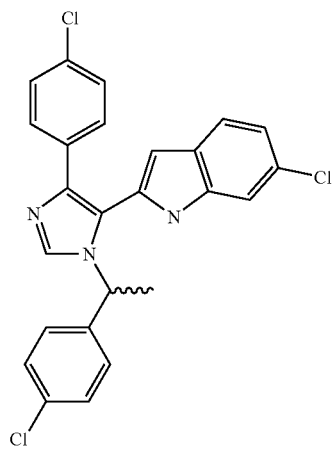
GI50~20 uM
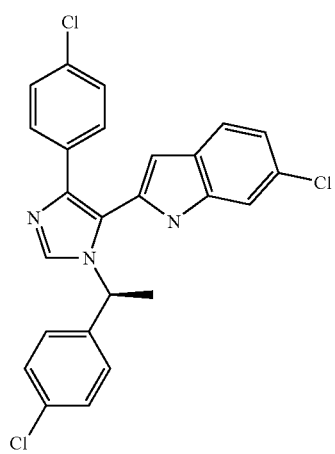
GI50~20 uM
TABLE 2-continued
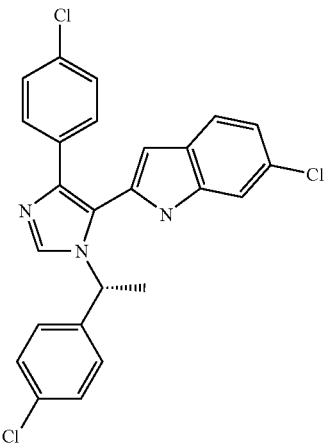
GI50~5 uM
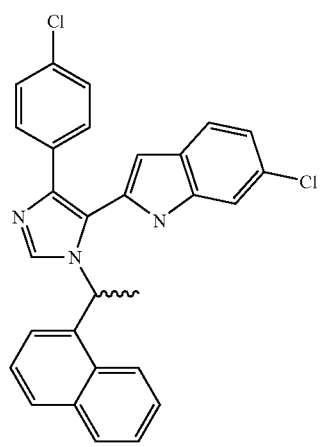
GI50~1 uM
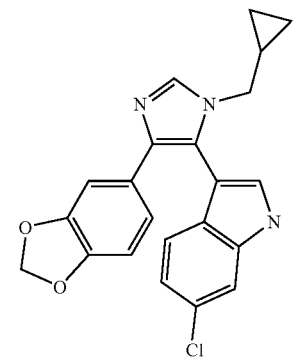
GI50~10 uM

TABLE 2-continued

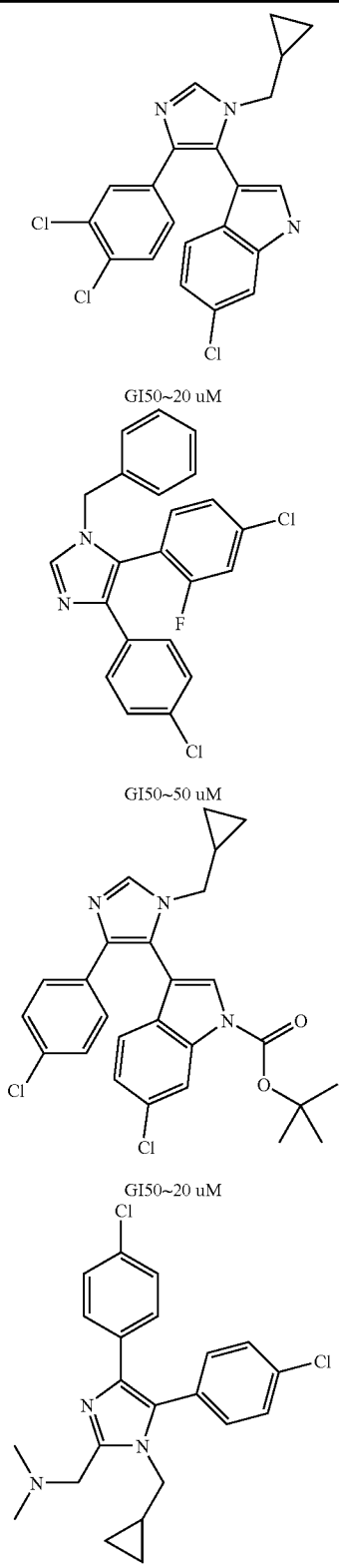

GI50~20 uM

GI50~50 uM

GI50~20 uM

Scaffold 2:
Preferred antagonists belonging to this chemotype have binding affinities ($K_A$) in the nM range. In this context at least two routes for optimizing the imidazolidine scaffold are proposed.

A straightforward approach for the facile synthesis of antagonists is to derivatize the carboxylic acid ester site. The carbonyl group of the ester is appropriately positioned for interaction with the Arg-residue of the p53 peptide. Modifications at this position of the imidazolidine scaffold could be used to increase the binding affinity as well as the water solubility of this class of molecules. In this aspect, the present invention provides a method for introducing a variety of lipophilic and water solubilizing groups, e.g., ethyl, propyl, cyclo-propylmethyl, 2-hydroxyethyl, 2-morpholinoethyl, 2-(hydroxymethyl)ethyl, 2-piperidinylethyl, 2-amino(N,N-diethyl)ethyl, and other similar groups into the imidazolidine scaffold. Additionally, substituents at imidazolidine 1-position, could be used to probe the above-mentioned hydrogen bonding interaction between the carbonyl group of Asn[72] and the bound analog. Optimization of compounds that belong to this family was carried out as shown in Scheme 12. Table 3 lists representative analogs that were synthesized with their GI50 values against HCT116 cells in culture. Further optimization at position-4 could also be done by the synthetic method of Scheme 2.

Scheme 12: Optimization route for Scaffold 2

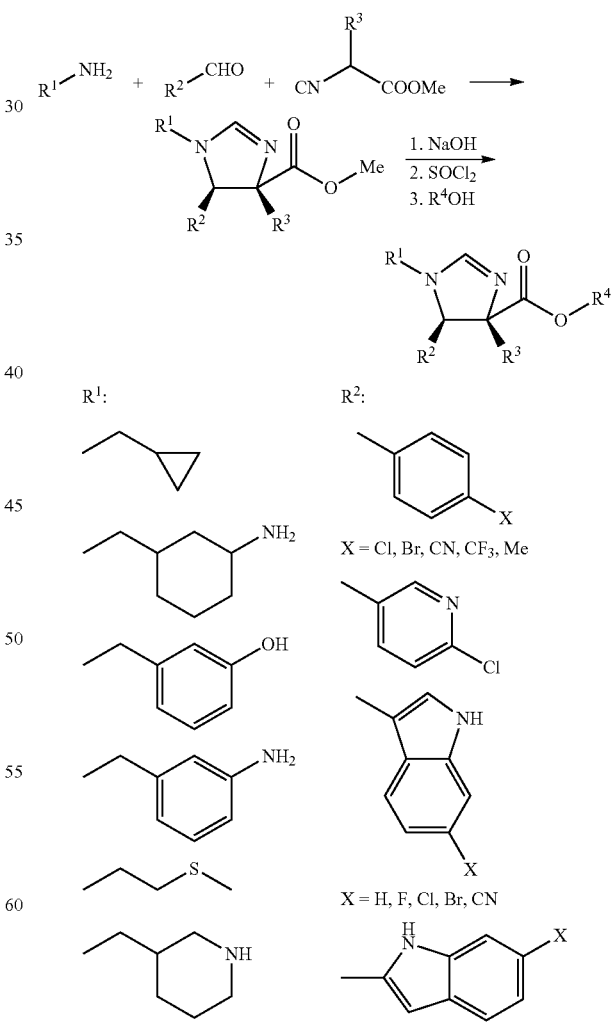

-continued
R³:
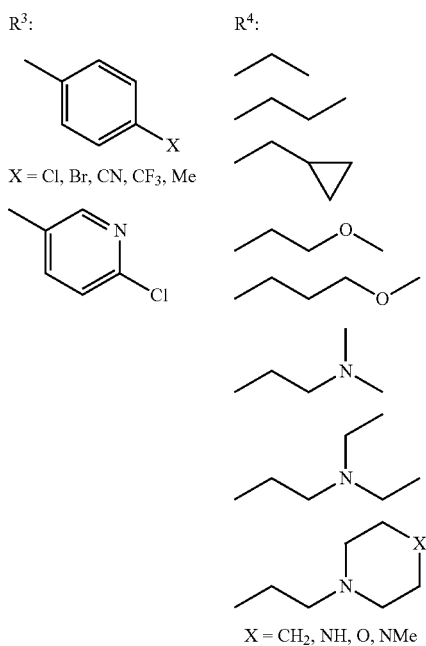
X = Cl, Br, CN, CF₃, Me
R⁴:
X = CH₂, NH, O, NMe
TABLE 3
Ki (mdm2)~10 uM
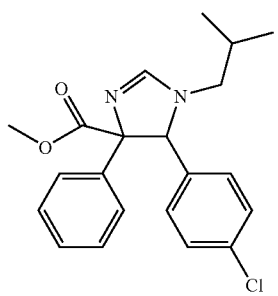
Ki (mdm2)~20 uM
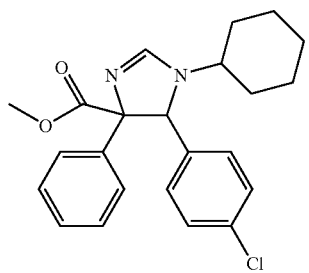
TABLE 3-continued
Ki (mdm2)~50 uM
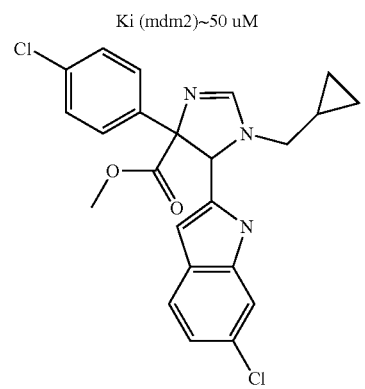
Ki (mdm2)~5 uM
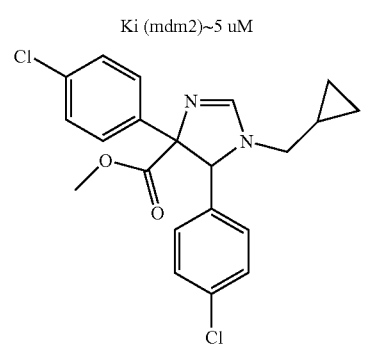
Ki (mdm2)~2 uM
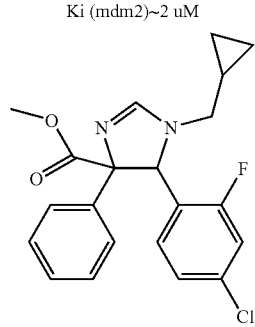
Ki (mdm2)~20 uM
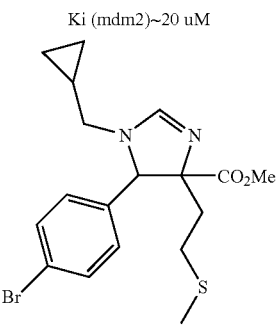

TABLE 3-continued
Ki (mdm2)~50 uM
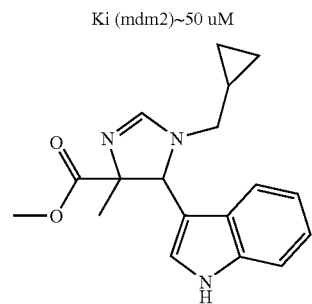
Ki (mdm2)~30 uM
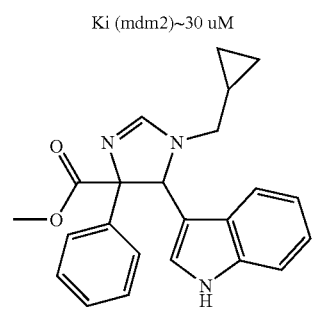
Ki (mdm2)~6 uM
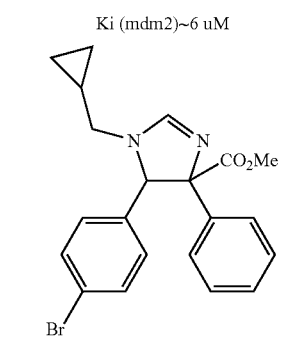
Ki (mdm2)~20 uM
Diastereomeric mix
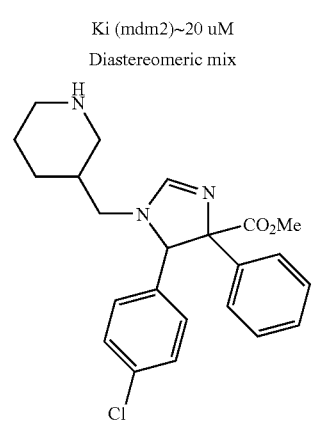
TABLE 3-continued
Ki (mdm2)~5 uM
Ki (mdm4)~5 uM
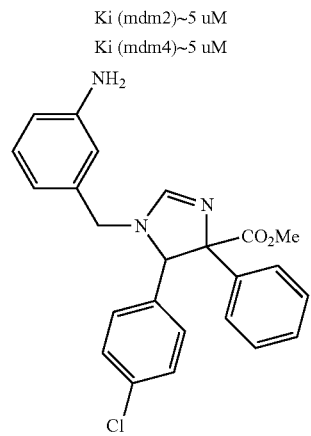
Ki (mdm2)~1 uM
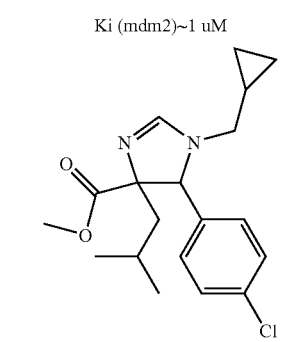
Ki (mdm2)~2 uM
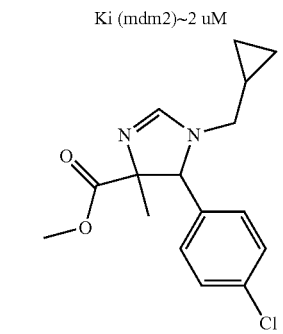
Ki (mdm2)~50 uM
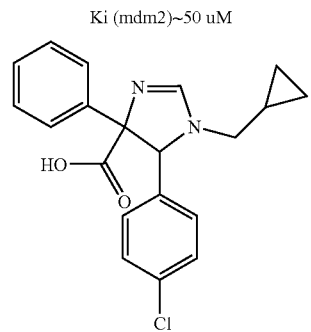

TABLE 3-continued
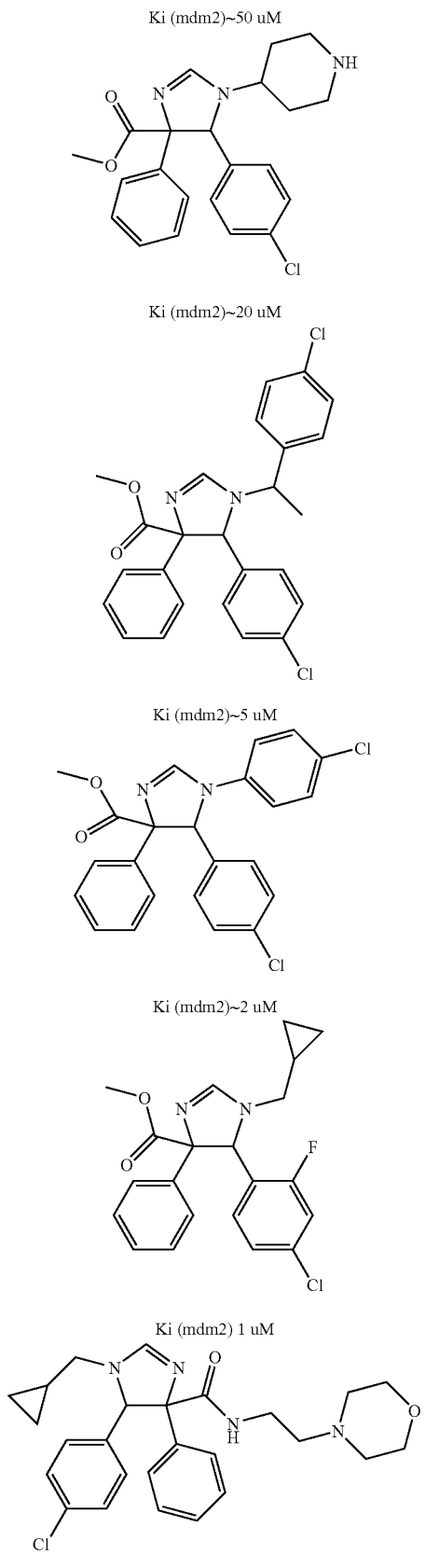
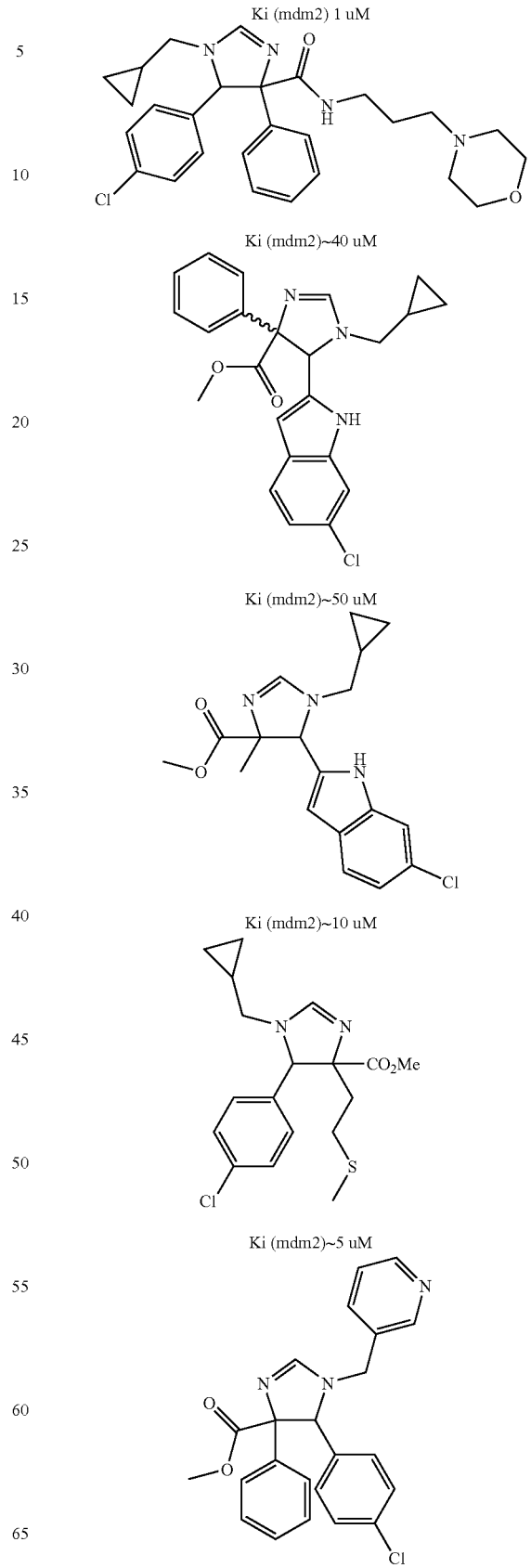

TABLE 3-continued

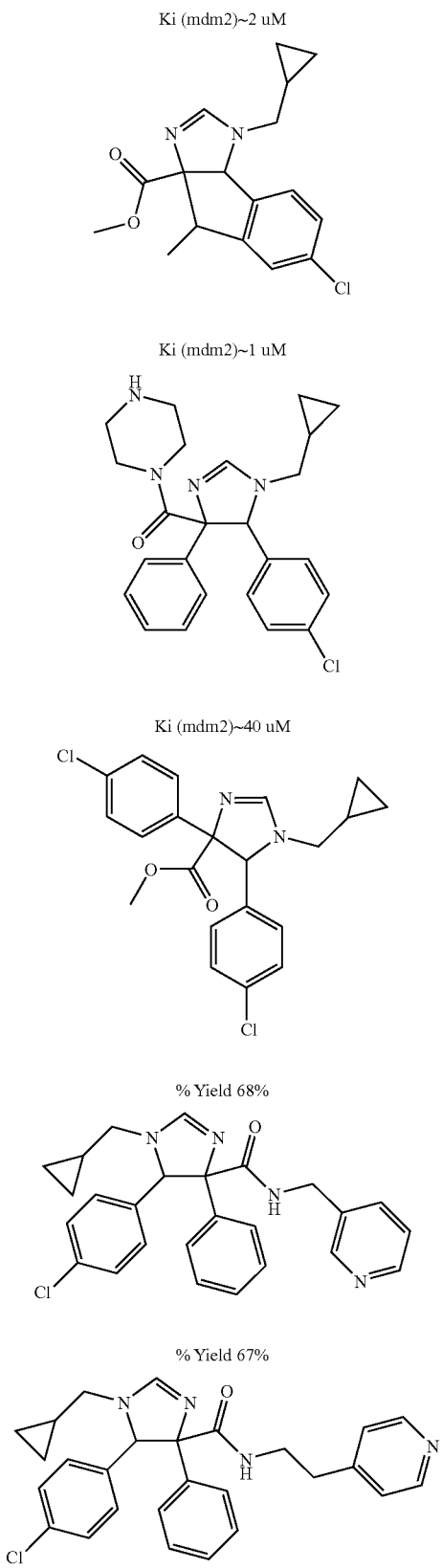

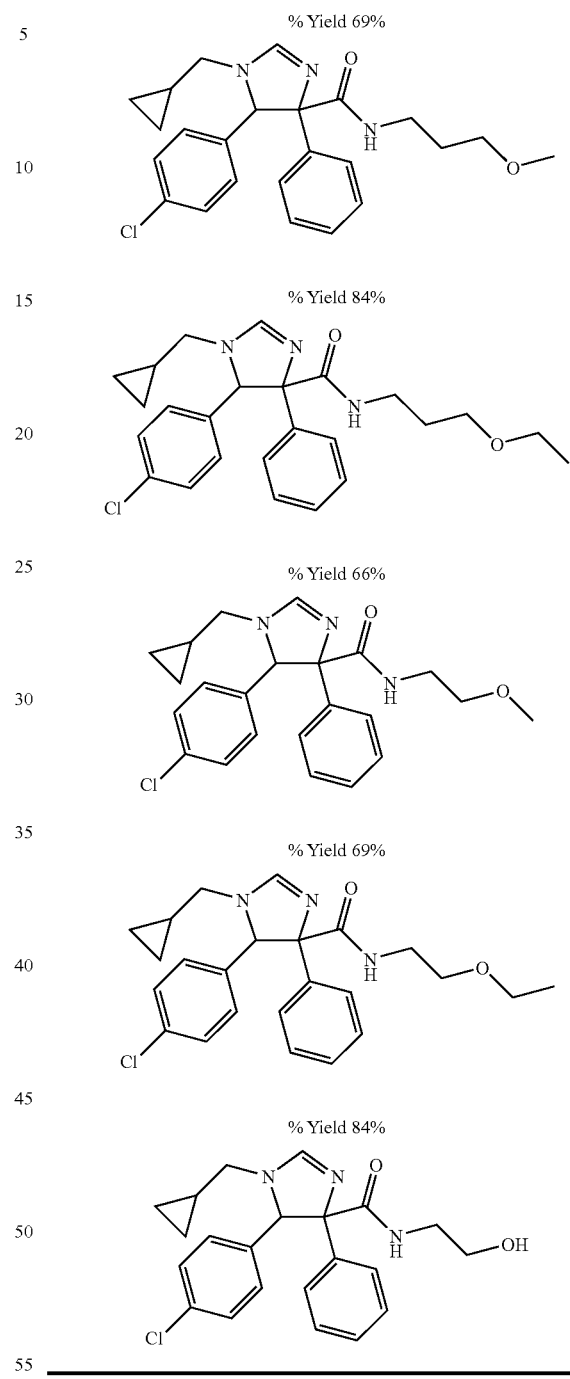

Scaffold 6:

NMR-based docking and preliminary binding assays have shown that the 1-(Alkylsulfonyl)-4,5-dihydro-1H-imidazole scaffold could be used to develop selective and dual-active MDM2/4 antagonists, in accordance with the invention. A suitable route for optimizing this scaffold are depicted in Schemes 11 and 13. The primary sulfonamides used for synthesizing the 1-(Alkylsulfonyl) imidazole analogs, can be synthesized from commercially available sulfonylchlorides using a published procedure.

Scheme 13. Optimization of the 1-(Alkylsulfonyl)-4,5-dihydro-1H-imidazole scaffold

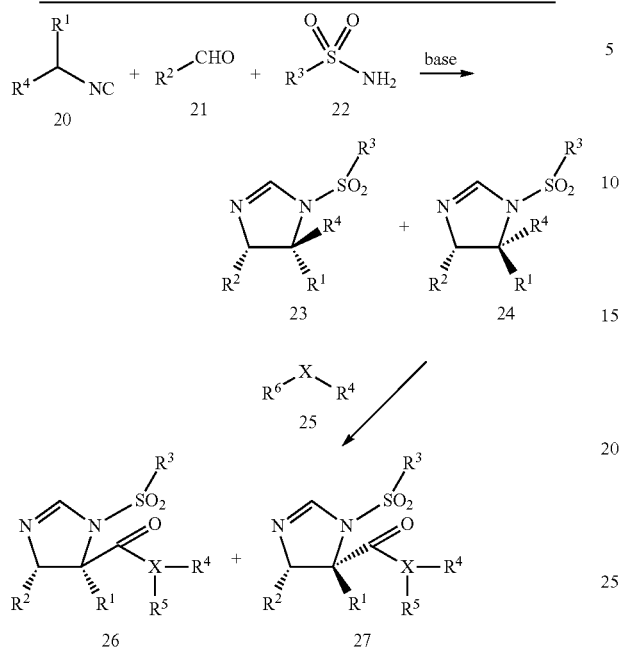

R1=R2=R3 is an optionally substituted alkyl, aroyl, heteroaroyl;
R4=R5 is H, alkyl, cycloalkyl;
R6=R7 is H, alkyl, cycloalkyl; and
X=O, N

What is claimed is:

1. A compound according to formula I

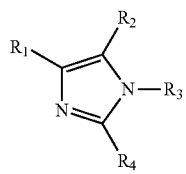

(I)

wherein said compound is an optionally substituted imidazole that antagonizes a MDM2/p53 or MDM4/p53 complex, wherein:

R1 is optionally substituted $(C_3-C_8)$aryl, $(C_3-C_8)$heterocycloalkyl, $(C_3-C_8)$ heteroaryl, $(C_1-C_6)$alkyl$(C_3-C_8)$aryl, $(C_3-C_8)$aryl$(C_1-C_6)$alkyl, optionally substituted benzyl, $(C_3-C_8)$cycloalkyl$(C_1-C_6)$alkyl and $(C_3-C_8)$cycloalkyl;

R2 is optionally substituted $(C_3-C_8)$aryl, optionally substituted $(C_3-C_8)$heteroaryl, optionally substituted $(C_3-C_8)$heterocycloalkyl, $(C_3-C_8)$heteroaryl$(C_1-C_6)$alkyl and $(C_3-C_8)$heterocycloalkyl$(C_1-C_6)$alkyl;

R3 is optionally substituted $(C_{3-8})$aryl, aryl$(C_1-C_6)$alkyl, optionally substituted benzyl, and $(C_3-C_8)$cycloalkyl $(C_1-C_8)$alkyl; and R4 is NRR'$(C_1-C_8)$alkyl; and R and R' are independently selected from the group consisting of hydrogen, $(C_1-C_8)$ alkyl and $(C_3-C_8)$cycloalkyl.

2. The compound according to claim 1, wherein the compound is

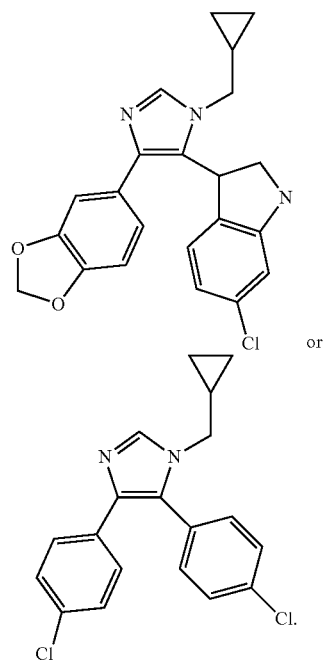

or

3. A compound according to formula II or its stereoisomer

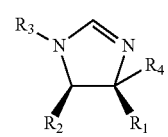

II wherein
R1 is straight or branched optionally substituted $(C_1-C_8)$ alkyl, optionally substituted $(C_3-C_8)$aryl, $(C_1-C_8$alkyl)-S—$(C_1-C_8$ alkylene), aryl$(C_1-C_6)$alkylene, $(C_3-C_8)$aryl $(C_1-C_6)$alkyl, optionally substituted benzyl, $(C_3-C_8)$cycloalkyl$(C_1-C_6)$alkylene, optionally substituted $(C_3-C_8)$aryl and $(C_3-C_8)$cycloalkyl;

R2 is optionally substituted $(C_3-C_8)$aryl, optionally substituted $(C_3-C_8)$heteroaryl, fused or unfused $(C_3-C_8)$heteroaryl;

R3 is optionally substituted $(C_1-C_8)$alkyl, optionally substituted $(C_3-C_8)$aryl, aryl$(C_1-C_6)$alkylene, optionally substituted benzyl, $(C_3-C_8)$cycloalkyl$(C_1-C_6)$alkylene, $(C_3-C_8)$cycloalkyl, $(C_3-C_8)$heterocycloalkyl, heteroaryl and $(C_3-C_8)$heterocycloalkyl$(C_1-C_6)$alkylene, $(C_3-C_8)$ cycloalkyl$(C_1-C_6)$alkylene, $(C_1-C_8$ alkyl)-X—$(C_1-C_8)$ alkylene;

X is O or N;

R4 is selected from the group consisting of C(O)OR, C(O) NR'R' and C(O)Z;

R is selected from the group consisting of hydrogen and $(C_1-C_6)$alkyl,

R' and R" are independently selected from the group consisting of hydrogen, $(C_1-C_8)$alkyl, $(C_1-C_8$ alkyl)-O—$(C_1-C_8)$alkylene, $(C_3-C_8)$cycloalkyl; $(C_1-C_8)$alkyl$(C_3-C_8)$heterocycloalkylene, $(C_3-C_8)$heteroaryl$(C_1-C_6)$ alkylene, (C$_3$-C$_8$)heterocycloalkyl and (C$_3$-C$_8$)heterocycloalkyl(C$_1$-C$_6$)alkylene; and
Z is a (C$_3$-C$_8$)heterocycloalkyl.
4. The compound according to claim 3, selected from the group consisting of
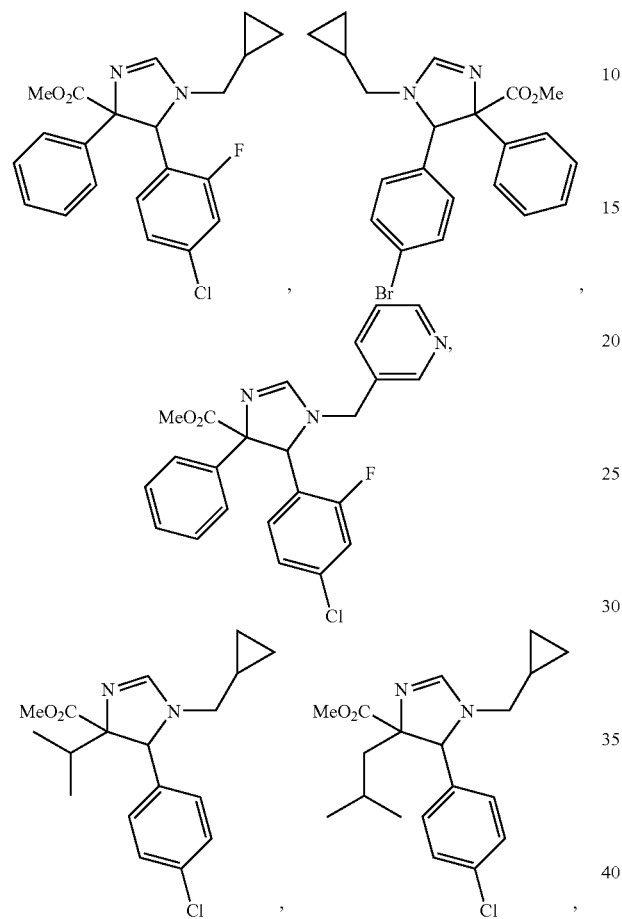
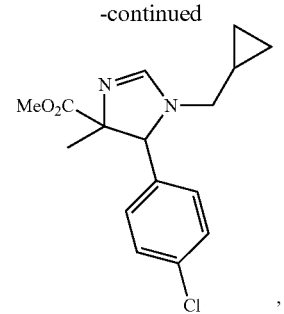
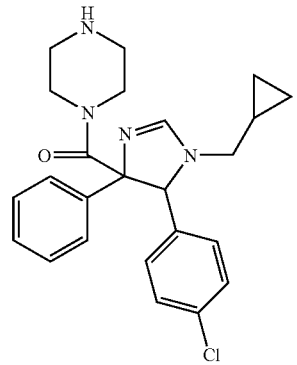
and
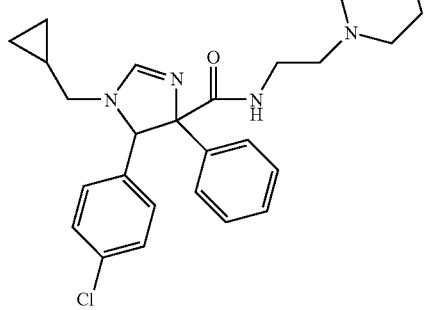
* * * * *